US00PP13593P3

(12) United States Plant Patent
Olesen et al.

(10) Patent No.: US PP13,593 P3
(45) Date of Patent: Feb. 25, 2003

(54) MINIATURE ROSE VARIETY 'POULGO003'

(76) Inventors: L. Pernille Olesen, Hillerødvejen 49, DK-3480 Fredensborg (DK); Mogens N. Olesen, Hillerødvejen 49, DK-3480 Fredensborg (DK)

( * ) Notice: Subject to any disclaimer, the term of this patent is extended or adjusted under 35 U.S.C. 154(b) by 21 days.

(21) Appl. No.: 09/776,155

(22) Filed: Feb. 2, 2001

(65) Prior Publication Data

US 2002/0152513 P1 Oct. 17, 2002

(51) Int. Cl.[7] ..... A01H 5/00

(52) U.S. Cl. ..... Plt./121

(58) Field of Search ..... Plt./118, 117, 116, Plt./119, 121, 122

*Primary Examiner*—Bruce R. Campell
*Assistant Examiner*—Annette H. Para

(57) ABSTRACT

A new miniature rose plant which has abundant, coral-pink flowers and attractive foliage. This new and distinct variety has shown to be uniform and stable in the resulting generations from asexual propagation.

1 Drawing Sheet

SUMMARY OF THE INVENTION

Classification:

*Botanical.*—*Rosa hybrida* 'POULgo003'.
*Commercial.*—Miniature.

The present invention constitutes a new and distinct variety of miniature rose plant which originated from a controlled crossing between an unnamed and unpatented variety, and 'POULrijk', described and illustrated in U.S. Plant Patent application Ser. No. 09/261,445, dated Mar. 3, 1999. The two parents were crossed during the summer of 1994 and the resulting seeds were planted in a controlled environment in Fredensborg, Denmark. The new variety is named 'POULgo003'.

The new variety may be distinguished from its seed parent, an unnamed seedling, by the following combination of characteristics:

1. 'POULgo003' has coral-pink flowers, whereas the seed parent has pink flowers.
2. 'POULgo003' exhibits pendulant to procumbent growth, while the seed parent has compact, upright growth.

The new rose may be distinguished from its pollen parent, 'POULrijk', by the following combination of characteristics:

1. 'POULrijk' is a ground cover shrub rose, whereas 'POULgo003' is a miniature rose.
2. 'POULrijk' has a spreading habit while 'POULgo003' exhibits a procumbent habit.
3. 'POULrijk' has semi-double, pure pink flowers, while 'POULgo003' has double, coral-pink flowers.

The objective of the hybridization of this rose variety was to create a new and distinct variety for garden use with unique qualities, such as:

1. Uniform and abundant flowers;
2. Vigorous, but compact growth when propagated by cuttings;
3. Disease resistance;
4. A miniature rose suitable for use in hanging basket containers in the nursery industry.

This combination of qualities is not present in previously available commercial cultivars of this type and distinguish 'POULgo003' from all other varieties of which we are aware.

As part of their rose development program, L. Pernille Olesen and Mogens N. Olesen germinated the seeds from the aforementioned hybridization during winter of 1994 and conducted evaluations on the resulting seedlings in a controlled environment in Fredensborg, Denmark.

'POULgo003' was selected in the spring of 1995 by the inventors as a single plant from the progeny of the aforementioned hybridization.

Asexual reproduction of 'POULgo003' by traditional budding and rooted cuttings was first done by L. Pernille and Mogens N. Olesen in their nursery in Fredensborg, Denmark in July 1995. This initial and other subsequent asexual propagations conducted in controlled environments have demonstrated that the characteristics of 'POULgo003' are true to type and are transmitted from one generation to the next.

BRIEF DESCRIPTION OF THE DRAWING

The accompanying color illustration shows as true as is reasonably possible to obtain in color photographs of this type the variety rose 'POULgo003'.

Specifically illustrated in SHEET 1 is a plant of 'POULgo003' growing in a 20-cm hanging basket.

DETAILED DESCRIPTION OF THE VARIETY

The following is a description of 'POULgo003', as observed in its growth in Jackson County, Oreg., on plants aged 18 months. Color references are made using The Royal Horticultural Society (London, England) Colour Chart, 1995, except where common terms of color are used.

For a comparison, several physical characteristics of the rose variety 'POULria', a rose variety from the same inventors described and illustrated in U.S. Plant Patent application Ser. No. 09/274,686 and dated Mar. 24, 1999 are compared to 'POULgo003' in Chart 1.

CHART 1

| | 'POULgo003' | 'POULria' |
|---|---|---|
| Color of open flower, outer side, middle zone. | Red-Purple Group 58C | Red Group 53A to Red-Purple Group 59C |
| Petalage | Double 25+ | Very double, 40–50 |
| Average Bloom Diameter | Small, 50–80 mm | Small, 35–40 mm |

Parents:

*Seed parent.*—Unnamed seedling.

*Pollen parent.*—'POULrijk'.

FLOWER AND FLOWER BUD

Blooming habit: Continuous.

Flower bud:

*Size.*—18 mm in length from base of receptacle to end of bud.

*Bud form.*—Long, pointed ovoid.

*Bud color.*—As sepals unfold, Red Group 43C and Red Group 50B; Red Group 43C and Red Group 50B at ¼ opening.

*Sepals.*—Shape: Sepal apex is cirrose; base is flat at union with peduncle. Length: 15 to 35 mm. Width: 8 to 9. Color: Upper surface is Yellow-Green Group 144 B and C. Lower surface is Yellow-Green Group 144 B and C. Appendages: Weak foliaceous appendages on 4 of the five sepals. Pubescence: Moderate. Stipitate Glands: Stipitate glands present on sepal margins.

*Receptacle.*—Surface: Glaucous. Shape: Funnel-shaped. Size: 5 mm (h)×6 mm (w). Color: Green Group 144B, with some anthocyanin intonation of Greyed-Purple Group 183D.

*Peduncle.*—Surface: Many stipitate glands and fine white hairs present. Length: 28 to 32 mm. Color: Yellow-Green Group 144B. Strength: Somewhat strong. Anthocyanin: Greyed-Purple Group 183D.

*Borne.*—2 to 3 buds per stem.

Flower bloom:

*Fragrance.*—Light, fresh scent.

*Duration.*—As a pot plant, flowers last from 12 to 15 days.

*Size.*—Small. Average flower diameter is between 40 to 45 mm when open.

*Form.*—Shape of flower when viewed from the side: Upon opening, upper part: Flattened convex. Upon opening, lower part: Flattened convex. After opening, upper part: Flattened convex. After opening, lower part: Concave.

*Petalage.*—Very double. Average range: 85 to 90 petals, with 10 to 15 petaloids.

Color:

*Upon opening, petals.*—Outermost petals: Upper surface: Red Group 55C. Lower surface: Red Group 55B. Innermost petals: Upper surface: Red Group 55C. Lower surface: Red Group 55CB.

*Upon opening, basal petal spots.*—Upper surface: Green-White Group 157C. Lower surface: Green-White Group 157C.

*After opening, petals.*—Outermost petals: Upper surface: Red Group 55B. Lower surface: Red Group 55C. Innermost petals: Upper surface: Red Group 55B. Lower surface: Red Group 55C.

*After opening, basal petal spots.*—Upper surface: Green-White Group 157C. Lower surface: Green-White Group 157C.

General tonality: On open flower, Red Group 43C. No change in the general tonality at the end of the 7$^{th}$ day. Afterwards, general tonality is Red Group 50B and C.

Petals:

*Petal reflex.*—Slight.

*Shape.*—Obovate.

*Petaloids.*—3 to 4. Petaloids are 5 to 7 mm long and 3 to4 mm wide. Petaloid coloration is Red Group 43B on both upper and lower surfaces.

*Thickness.*—Average.

*Arrangement.*—Imbricated.

Reproductive organs:

*Filaments.*—Color: Yellow-Green Group 154D. Length: 4 mm.

*Pistils.*—Length: 7 mm. Quantity: 30 to 35.

*Pollen.*—Color: Yellow Group 12B. Quantity: Average.

*Anthers.*—Length: 1 mm. Color: Brown Group 200C. Quantity: 20.

*Stigmas.*—Height: Stigmas are even in height relative to anthers. Color: Greyed-Green Group 196D.

*Styles.*—Color: Greyed-Green Group 192A. Length: 4 mm.

*Hips.*—None observed.

PLANT

Plant growth: Compact, spreading growth. Average height of the plant is 40 cm; the average width is 30 cm.

Stems:

*Color.*—Young wood: Yellow-Green Group 144B. Older wood: Yellow-Green Group 144A and B.

*Thorns.*—Incidence: 10 to 12 thorns per 10 cm of stem. Size: Average length is 3 mm. Color: Greyed-Yellow Group 160D. Shape: Linear.

*Surface.*—Older wood: Smooth. Young wood: Smooth.

Plant foliage:

*Number of leaflets on normal leaves in middle of a stem.*—5.

*Leaf size.*—60 mm (l) by 40 mm (w).

*Quantity.*—Average.

*Glossiness.*—Upper side weak glossiness.

*Color.*—Mature foliage: Upper Leaflet Surface: Yellow-Green Group 146A. Lower Leaflet Surface: Yellow-Green Group 146C. Juvenile foliage: Upper Leaflet Surface: Yellow-Green Group 146A. Lower Leaflet Surface: Yellow-Green Group 146C. Anthocyanin intonation: Greyed-Red Group 185A on margins of upper leaflet surface, all of lower surface, petiole, rachis, and stipule.

Plant leaflets:

*Stipule.*—Size: 10 mm (l)×4 mm (w). Color: Yellow-Green Group 144B and C. Anthocyanin: Greyed-Red Group 183C. Stipitate Glands: On edges of stipules.

*Petiole.*—Length: 7 mm. Color: Yellow-Green Group 144B. Underneath: Yellow-Green Group 144B. Stipitate glands and occasionally a single, small thorn. Margins: Yellow-Green Group 144A. Anthocyanin: Greyed-Red Group 183C.

*Rachis.*—Color: Yellow-Green Group 144B. Underneath: Yellow-Green Group 144B. Stipitate glands and occasionally a single, small thorn. Margins: Yellow-Green Group 144A. Stipitate glands present. Anthocyanin: Greyed-Red Group 183C.

*Leaflet*.—Edge: Dentate. Shape: Ovate. Surface: Moderately glossy. Texture: Leathery. Arrangement: Odd pinnate. Venation: Reticulate.

Disease resistance: Above average resistance to mildew, rust, black spot, and Botrytis under normal growing conditions in Jackson County, Oreg.

Cold hardiness: The variety 'POULgo003' has been found to be resistant to damage from cold in USDA Zone 7.

We claim:

1. A new and distinct variety of rose plant of the miniature rose class, substantially as herein illustrated and described as a distinct and novel rose variety due to its abundant coral-pink flowers, procumbent to arching habit, disease resistance, and extended period of bloom.

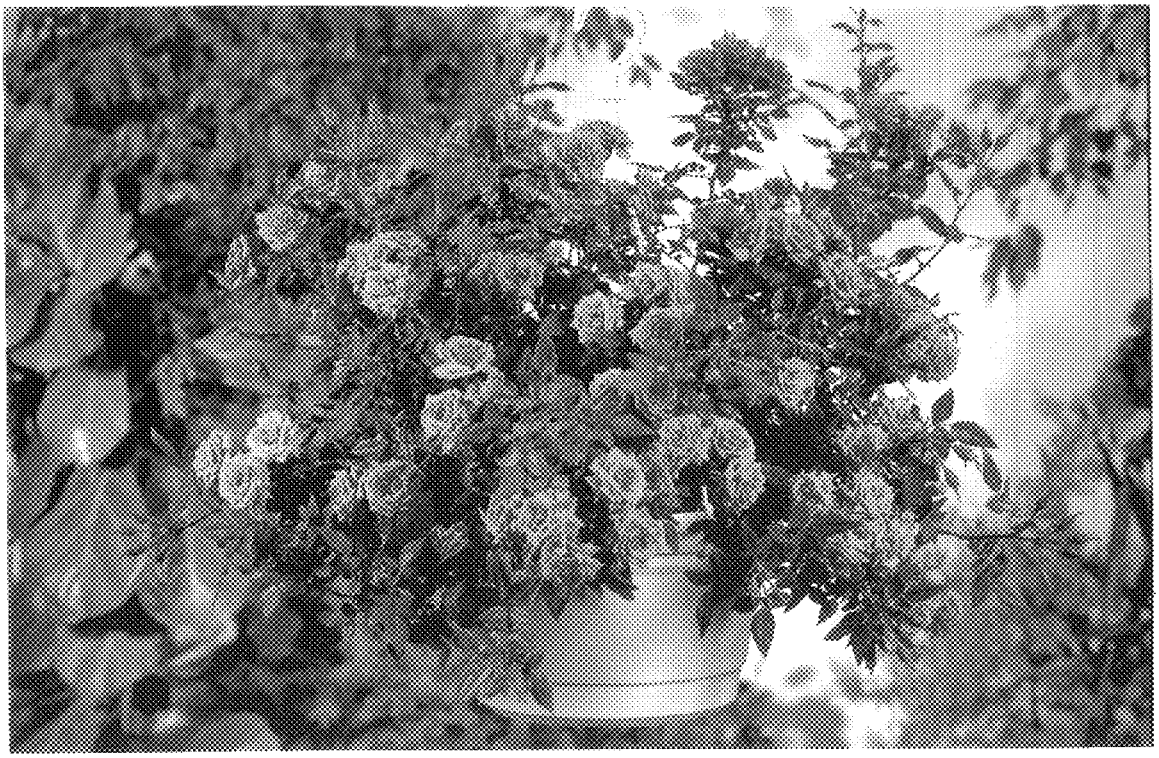

* * * * *